United States Patent [19]
Nelson et al.

[11] Patent Number: 6,153,181
[45] Date of Patent: Nov. 28, 2000

[54] GRANULAR PEST BAIT

[75] Inventors: Thomas D. Nelson, Maplewood; Douglas G. Anderson, Lakeville; S. John Barcay, Burnsville, all of Minn.

[73] Assignee: Ecolab Inc., St. Paul, Minn.

[21] Appl. No.: 09/389,897

[22] Filed: Sep. 3, 1999

[51] Int. Cl.[7] .......................... A01N 25/00; A01N 37/18; A01N 43/04; A01N 57/12; A01N 59/14
[52] U.S. Cl. .......................... 424/84; 424/405; 424/409; 424/489; 424/491; 424/493; 424/499; 424/502; 424/535; 424/659; 514/2; 514/23; 514/53; 514/118; 514/120; 514/951
[58] Field of Search ................ 424/84, 405, 489, 424/499, 502, 535, 195.1, 659, 409, 410, 491, 493; 514/53, 23, 137, 75, 2, 118, 120, 951; 43/121, 132.1; 426/1

[56] References Cited

U.S. PATENT DOCUMENTS

| | | | |
|---|---|---|---|
| 4,205,066 | 5/1980 | Hennart et al. | 424/84 |
| 4,313,940 | 2/1982 | Pasarela | 514/144 |
| 4,834,977 | 5/1989 | Kohama et al. | 424/405 |
| 4,985,413 | 1/1991 | Kohama et al. | 514/79 |
| 4,988,511 | 1/1991 | Demetre | 424/84 |
| 5,300,293 | 4/1994 | Minagawa et al. | 424/405 |
| 5,464,613 | 11/1995 | Barcay et al. | 424/84 |
| 5,484,587 | 1/1996 | Branly et al. | 424/84 |
| 5,484,588 | 1/1996 | Ogino et al. | 424/84 |
| 5,820,855 | 10/1998 | Barcay et al. | 424/84 |
| 5,850,707 | 12/1998 | Fell et al. | 43/131 |
| 5,914,105 | 6/1999 | Barcay et al. | 424/84 |

OTHER PUBLICATIONS

JP 62198602 A (Sep. 2, 1987), 'Insecticidal granule, used in control of rice weevil', Acc. No. 1987–286910, WEST online, file DWPI, Abstract.
Zhang, CN 1092597 A (Sep. 28, 1994), 'Pesticide granules for cockroaches', Acc. No. 1997–166317, WEST online, file DWPI, Abstract.
Appel, A. G., "Performance of Gel and Paste Bait Products for German Cockroach (Dictyoptera: Blattellidae) Control: Laboratory and Field Studies," *Entomological Society of America*, vol. 85, No. 4, 10 pp. (1992).
Reierson, D. A. et al., "Baits and Bait Technology," *Proceedings of the National Conference on Urban Entomology*, pp. 77–91 (1992).
Rust, M. K., "Managing Household Pests," *Advances in Urban Pest Management*, pp. 335–368 (1986).
Manufacturer's Brochure, "ECO2000–FB," 3 pp. (1999).
Material Safety Data Sheet, "Maxforce," 1 p. (1963).

*Primary Examiner*—John Pak
*Assistant Examiner*—Frank Choi
*Attorney, Agent, or Firm*—Merchant & Gould P.C.

[57] ABSTRACT

Disclosed is a substantially water-free insecticidal granular bait suitable for controlling crawling insects such as cockroaches and ants. The bait includes an insecticide, several feeding stimulants which are typically carbohydrates and proteins, and a lipid. These bait compositions are in granular form, which are useful for application in hard-to-reach areas and are particularly useful in wet conditions, as well as hot, dry areas.

19 Claims, 6 Drawing Sheets

Efficacy of Borid Dust
(99.0% boric acid, 15 minute exposure)
against Male German Cockroaches

GRANULAR PEST BAIT

FIELD OF THE INVENTION

This invention relates to a substantially water-free, granular pest bait for controlling insects, particularly cockroaches and ants.

BACKGROUND OF THE INVENTION

Historically, toxic baits for controlling crawling insects such as cockroaches have been water-based. With cockroaches especially, water is presumed necessary for good bait performance. Unfortunately, water-based bait products rapidly lose effectiveness due to water loss, rancidity, breakdown of active ingredients and other factors. Studies of water-based paste baits have confirmed that water loss, repellant properties of active ingredients, and insecticide resistance are the most important factors affecting bait performance. Appel, A. G., *J. Econ Entomol.* 85 (4):1176–1183 (1992), Robinson, W. H., *Proceedings of the National Conference on Urban Entomology* 77–91 (1992), and Rust, N. K., "Managing Household Pests", in *Advances in Urban Pest Management,* G. W. Bennett and M. Owens (eds), Van Norstrand Reinhold, N.Y. 335–368 (1986).

One approach to improve on water-based insecticide products has been to use a dust or paste composition which contains a so-called water powder with the insecticide. This water powder is water entrapped within hydrogenated soybean oil, as described in U.S. Pat. No. 5,820,855. Another water-free fat-based pest bait product is described in U.S. Pat. No. 5,464,613. These compositions are paste forms and includes as a major ingredient a fat-based carrier. Unfortunately, dust compositions have disadvantages such as drifting of the material when applied. Although paste products do not drift, they can be difficult to apply and require an applicator for applying pastes in cracks and crevices. Additionally, paste bait products cannot be easily and effectively applied into void areas which can be major pest harborage areas. Also, paste baits can rapidly lose water in hot, dry areas and become ineffective. There is thus a need for improved pesticide compositions especially for use in wet or moist areas, as well as in hot, dry void areas.

SUMMARY OF THE INVENTION

The present invention provides a substantially water-free product which is easy to apply in cracks, crevices and voids. The invention is a granular, substantially water-free, pest bait, which is useful in hard-to-get-at areas and particularly useful in wet or moist areas, and also in hot, dry void areas.

Insecticides in granular form according to the present invention show faster kill than corresponding pastes or dust formulations. The granular composition of the present invention is characterized by having a critical load of less than 1 Newton (N). The critical load is a measure of the granule's crushability. The present invention has particle sizes ranging from about 0.4 to about 2 millimeters (mm) in diameter.

Accordingly, the invention is found in a substantially water-free granular insecticide composition including an effective amount of an insecticide, a sufficient amount of lipid, and the balance being feeding stimulants including a carbohydrate and a protein, wherein the granules range in size from about 0.4 to about 2.0 mm and have a critical load when crushed of less than 1 N.

As a particular embodiment, the invention is found in an insecticide composition including in granular form at least about 40 weight percent (wt-%) boric acid, up to about 25 wt-% lipid, preferably about 5 to 15 wt-% lipid, and the balance being feeding stimulants containing a carbohydrate and a protein.

In another particular embodiment, the invention is found in an insecticide composition including in granular form at least about 0.1 weight percent (wt-%) acephate, up to about 25 wt-% lipid, preferably about 5 to 15 wt-% lipid, and the balance being feeding stimulants containing a carbohydrate and a protein.

The invention is also found in methods of controlling pests which include application of the granular compositions previously described.

DETAILED DESCRIPTION OF THE INVENTION

The invention involves an essentially water-free insecticidal granular bait composition which includes an insecticide including, for example, boric acid or acephate along with feeding stimulants and a lipid. The insecticide is the active ingredient which serves to kill the insect, while the feeding stimulants serve to attract the insect to the bait and entice it to eat. The feeding stimulants include carbohydrates and proteins. The lipid serves as an additional feeding stimulant and also helps protect the composition from water. Useful boric acid composition ranges are described in Table 1 while useful acephate composition ranges are shown in Table 2:

TABLE 1

| Ingredient | Useful (wt-%) | Preferred (wt-%) |
| --- | --- | --- |
| boric acid | >40 | 40–60 |
| fat | <25 | 5–15 |
| feeding stimulant | balance | balance |

TABLE 2

| Ingredient | Useful (wt-%) | Preferred (wt-%) |
| --- | --- | --- |
| acephate | >0.1 | 0.1–5 |
| fat | <25 | 5–15 |
| feeding stimulant | balance | balance |

A particularly useful boric acid composition is given below in Table 3, while Table 4 describes a preferred acephate composition:

TABLE 3

| Ingredient | Weight Percent |
| --- | --- |
| boric acid | 52.73 |
| soybean oil | 9.09 |
| powdered sugar | 23.45 |
| whole milk powder | 14.73 |

TABLE 4

| Ingredient | Weight Percent |
| --- | --- |
| acephate | 1.00 |
| soybean oil | 10.00 |
| powdered sugar | 25.00 |
| whole milk powder | 64.00 |

Insecticide

A variety of insecticides can be used in the granular composition of the present invention. Examples of insecticide compounds useful in the invention include those found in the following classes:

1-organophosphates, e.g. acephate, chlorpyrifos or diazinon;

2-mineral acids, e.g. boric acid;

3-carbamates, e.g. propoxur, 2-(1,3-dioxolane-2-yl)-phenyl-N-methylcarbamate;

4-pyrethroids, e.g. cyfluthrin;

5-amidinohydrazones, e.g. hydramethylnon;

6-avermectins, e.g. abamectin;

7-chlorinated hydrocarbons, e.g. lindane, and combinations of these with known synergists, e.g. o-isoproxy-phenylmethyl-carbamate or 2-(1,3-dioxolane-2-yl)-phenyl-N-methylcarbamate may be combined with piperonyl butoxide or piperonal bis-(2,2-butoxyethoxy)-ethyl) acetal. Preferred insecticides include boric acid and acephate.

Boric acid can be used as an active ingredient in the claimed insecticidal bait composition. Boric Acid Technical Powder is a white, crystalline product available from U.S. Borax, Inc. The boric acid, which has a molecular formula of $H_3BO_3$, is used at a minimum content of at least about 40 wt-%. Preferably, it is used at a concentration of about 40 to about 60 wt-%.

Acephate can also used be used as an active ingredient in the claimed insecticide composition. Acephate is a fine crystalline powder that is water soluble and can be easily incorporated into a fat by forming a suspension or paste. It is a desirable active ingredient because there is no known insecticide resistance and it has very low mammalian toxicity. Acephate has a molecular formula of $C_4H_{10}NO_3PS$ and is typically used at a minimum content of about 0.1 wt-%. A preferred range is a concentration of about 0.1 to about 5 wt-%.

Lipids

Lipids are included both as a minor feeding stimulant and more importantly to protect the composition from water. A major portion of the composition contains lipids present as glycerides and falling within a definition of lipids as being "A glycerol ester of fatty acid(s): Fats/lipids generally are substances of plant and animal origin. Fat may be in a solid form, as tallow, lard, butter, margarine or other shortenings or in liquid form, e.g., as vegetable oils." Certain vegetable oils can also be solid depending on the degree of hydrogenation or saturation.

The glycerol esters are predominantly of the triglyceride type; vegetable oils and fats may also contain some di- and even mono-glycerides. The fatty acid component of fats and vegetable oils encompass the range of fatty acids containing from about 8–22 carbon atoms, preferably in the range of 12 to 18 carbon atoms. Although most of the fatty acid content is saturated linear alkonoic acid, some of the fatty acid content may be unsaturated, as exemplified by oleic and linoleic acid.

Examples of preferred fats and oils used in the present invention are partially hydrogenated vegetable oil including soy bean and cottonseed oil mixtures in solid or liquid flake form, partially hydrogenated cottonseed oil in solid form, partially hydrogenated soybean oil in solid form, partially hydrogenated vegetable oil containing a mixture of palm kernel and coconut oils in liquid form, partially hydrogenated nonvegetable coconut oil in liquid plastic form, partially hydrogenated vegetable oil in liquid flake form having a mixture of a palm kernel and cottonseed with lecithin, hydrogenated cottonseed oil, hydrogenated palm oil, hydrogenated soybean oil, hydrogenated vegetable oil in liquid form containing a mixture of grapeseed, cottonseed and soybean oil, partially hydrogenated vegetable oil containing a mixture of soybean and palm oil with vegetable mono and diglycerides and Tween 60K, in plastic form, partially hydrogenated vegetable oil containing soybean, cottonseed with vegetable mono and diglycerides in plastic form, partially hydrogenated vegetable oil in paste or margarine type of form which contains a mixture of soybean and cottonseed oils with water, salt, nonfat milk, lecithin, mono and diglycerides, sodium benzoate, artificial color, artificial flavor, vitamin A palmitate, soybean oil, corn oil, coconut oil, mono and diglycerides, ethoxylated mono and diglycerides, polyglycerol esters of fatty acids, and polyglycerol as fatty acids.

Preferred lipids are those considered to be vegetable oils. Particularly preferred is soybean oil. Because of the nature of the granular compositions of the present invention, the amount of lipid used is equal to or less than about 25 wt-% of the total weight of the composition, and is preferably at a concentration of about 5 to about 15 wt-%.

Feeding Stimulants

Feeding stimulants are included in the composition to attract the insect to the bait, and to entice the insect to eat the bait. Preferable feeding stimulants include mixtures of carbohydrates and proteins. Examples of carbohydrates are maltodextrins and the like; carbohydrate complexes, corn syrup solids, sugars such as sucrose, glucose, fructose, starches such as corn, potato and the like. Examples of proteins include yeast extracts and milk solids, e.g. whole milk powder. The feeding stimulants constitute the balance of the composition depending on the of insecticide and lipid employed. Preferred stimulants are a mixture of powdered sugar and milk solids, e.g. whole milk powder. Powdered sugar is a food grade product made by grinding granulated sugar with corn starch. Powdered sugar contains about 97 wt-% sucrose and about 3 wt-% of corn starch.

Optional components

These can include additional attractants. Examples of attractants are odorants and flavorants such as, for example, cyclotenes and the like, plant extracts such as fenugreek and the like, alcohols such as ethanol, or a volatile ester in combination with ethanol. Said volatile ester is made from a combination of a $C_1$–$C_6$ branched or unbranched alcohol with a $C_1$–$C_3$ carboxylic acid. Lower alcohols useful in the manufacture of the volatile ester co-attractants of the invention include methyl alcohol, ethyl alcohol, n-propyl alcohol, isopropyl alcohol, n-butyl alcohol, isobutyl alcohol, tertiary butyl alcohol, n-amyl alcohol, isoamyl alcohol, tertiary amyl alcohol, n-hexyl alcohol, and mixtures thereof, etc. Carboxylic acids useful in manufacturing the ester attractant of the invention include acetic acid, propionic acid, butyric acid, mixtures thereof, and others. The associated reactive analogs of the respective carboxylic acids can be used, for example, the acid chloride or acid anhydride. The preferred volatile ester for use is a lower alcohol acetate ester such as n-amyl acetate, isoamyl acetate, isobutyl acetate, n-propyl acetate, ethyl acetate or mixtures thereof. some of the ingredients may overlap in category as they can be both attractants and feed stimulants, for example proteins mentioned above, odorants and flavorants.

Processing

The insecticide composition of the invention can be made by combining the boric acid (or acephate) and feeding stimulants and blending thoroughly. Once blended, the mixture is transferred to a roller compactor/granulator with a mesh screen for the desired particle size. Preferred is a 10 mesh screen. After granulation, the granulated blend is transferred to a ribbon mixture, where the fat is slowly added with simultaneous mixing. The resulting granular composition has granules ranging in size from about 0.4 to about 2.0 mm. Such granules when crushed exhibit a critical load of less than about 1 N. Critical load is measured by placing a granule in a crush test equipment and examining the pressure load on the granule as a function of time. Critical load is the point at which a clear load drop is observed.

The following examples are intended to illustrate the invention but are not to be construed as limiting the invention.

WORKING EXAMPLES

Example 1

This example describes a sample formulation illustrative of the invention. A granulated insecticide composition was prepared according to the following guidelines.

| Ingredient | Weight Percent |
|---|---|
| boric acid | 52.73 |
| salad oil | 9.09 |
| powdered sugar | 23.45 |
| whole milk powder | 14.73 |

1. The boric acid, powdered sugar and whole milk powder were combined in a Ribbon mixer and were thoroughly blended.

2. The resulting blend was transferred to a roller compactor/granulator, where it was compacted and granulated using a 10 mesh screen.

3. The granulated blend was transferred to a Ribbon mixer, where salad oil was slowly poured in while the mixer was running.

Example 2

This example describes crush testing performed on the granular product of the present invention. For comparison purposes, a presently available commercial product, a fine granular matrix containing hydramethylnon, was also tested.

The two materials were crush tested in an apparatus known as the Micro-Mechanical Tester (MMT). As this is not a commercial product, no manufacturers specifications exist. This instrument has a load resolution of about 50 to 100 $\mu$N and a maximum load of about 5 N. Each granule was examined in an optical microscope and two measurements were made to estimate the mean diameter.

Figure 1:
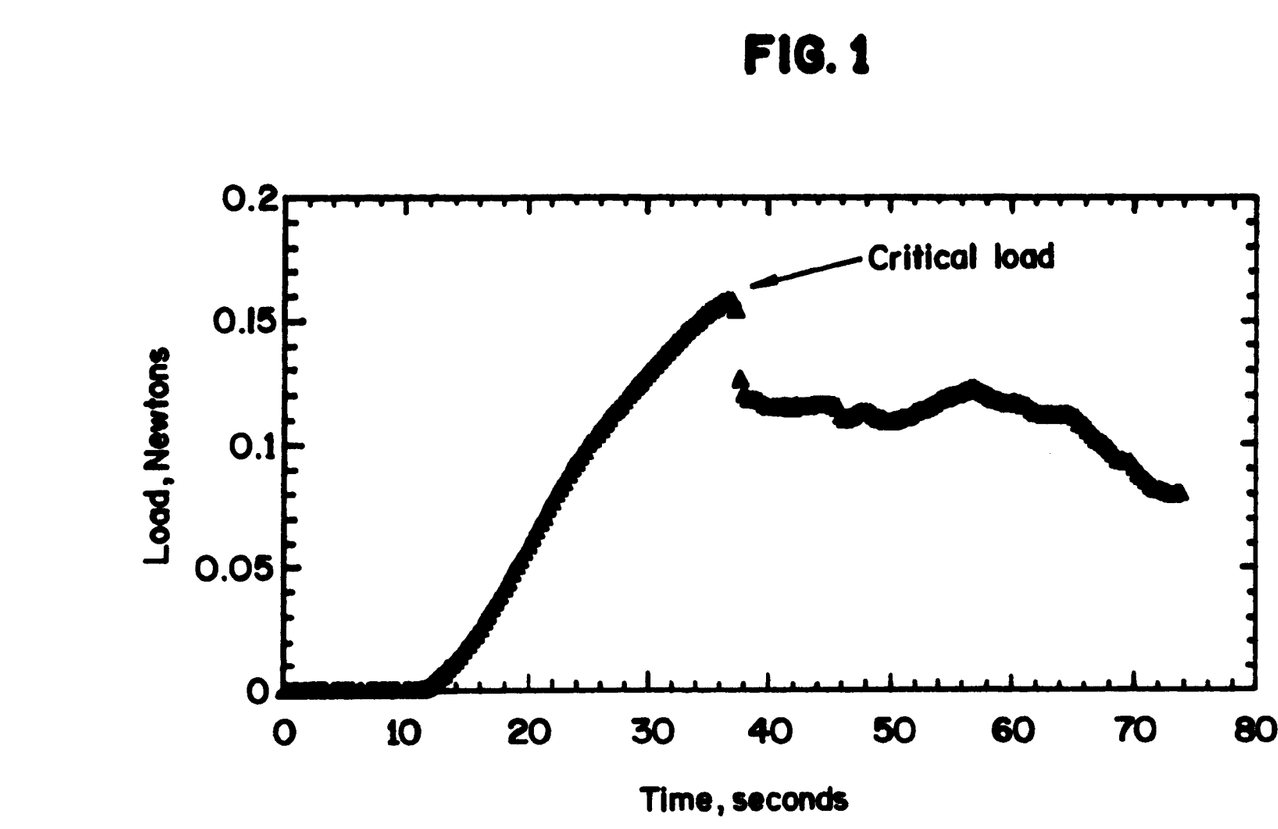
FIG. 1 is a plot of load versus time for the granular pest bait of the present invention, demonstrating the critical load.

The granules were then crushed in the MMT by placing them between two steel cylinders and subsequently driving the two cylinders together at a rate of 1 $\mu$m per second. A computer was used to continuously collect the applied force. By examining the load as a function of time (see FIG. 1, for example, which provides this data for the specimen representing the present invention), a clear load drop was seen. At this point, the specimen has typically broken into at least two distinct pieces.

Figure 2:
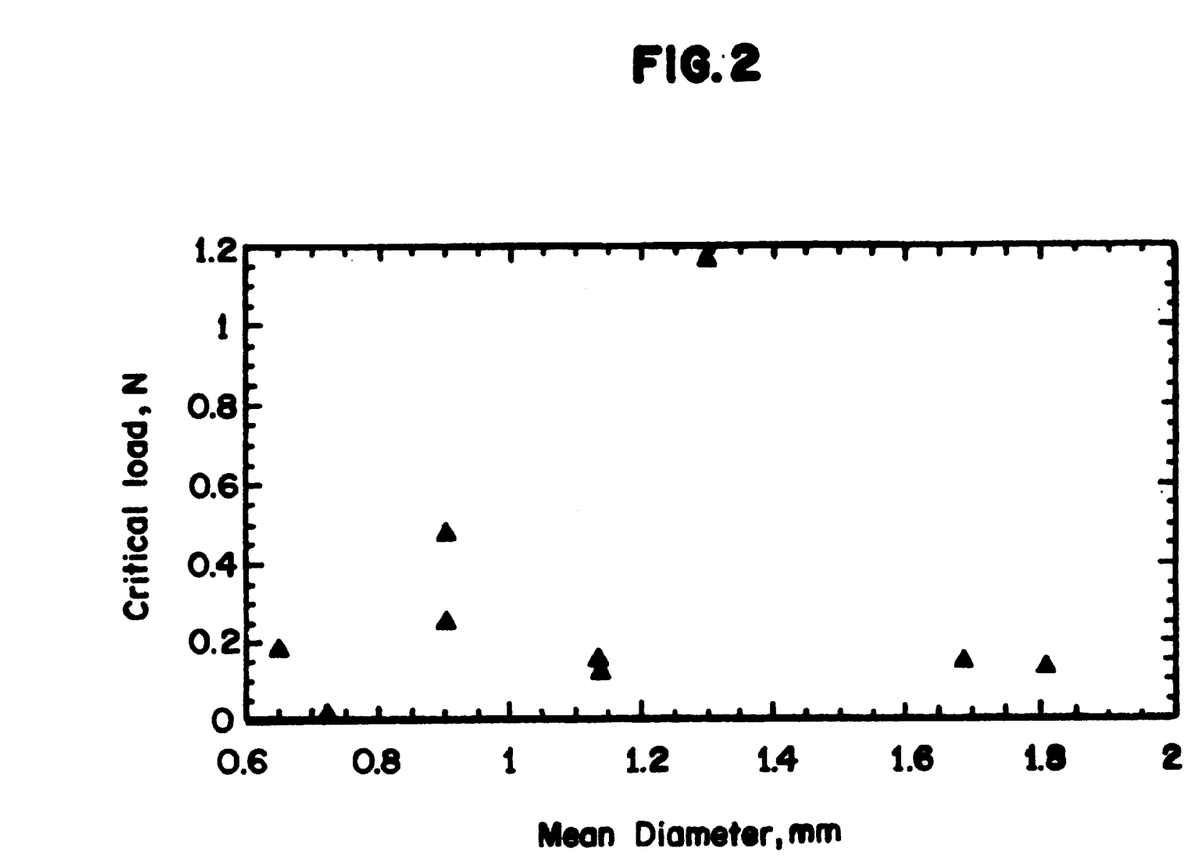
FIG. 2 is a plot of critical load versus particle diameter for the granular pest bait of the present invention.

FIG. 2 shows critical load as a function of granule diameter for the specimen representing the present invention. No particular trend is seen in this data. The load to failure ranged from 0.017 to 1.17 N with a mean value of 0.298 N and a standard deviation of 0.350 N.

Figure 3:
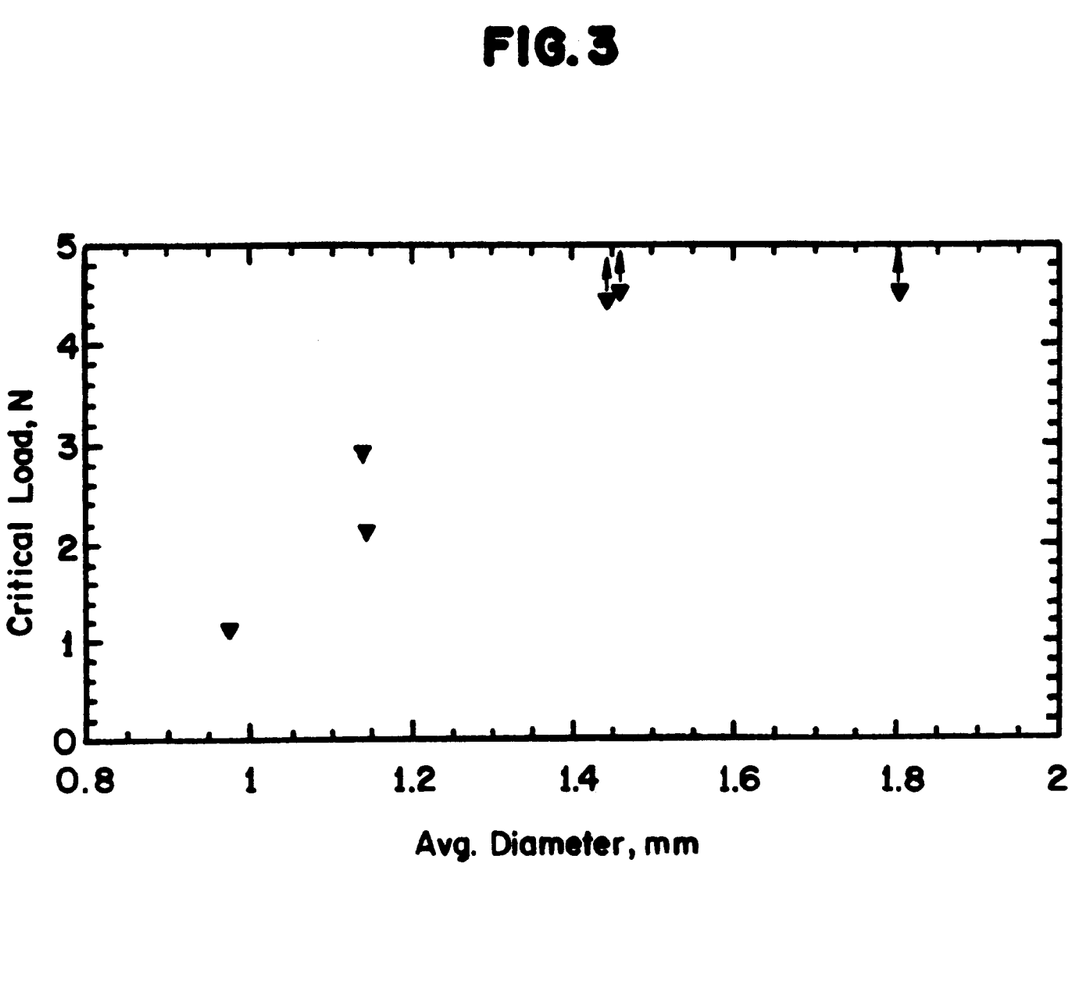
FIG. 3 is a corresponding plot of critical load versus particle diameter for a commercial product used for comparison purposes.

FIG. 3 shows the corresponding results for the samples of a commercially available ant bait consisting of a fine granular matrix containing hydramethylnon. Four particles were tested using a low range load cell, and all four went out of range without crushing. Six more particles were tested using a maximum range load sensor, and three of these particles still exceeded the range of the test sensor. The above fine granular samples appear to demonstrate a linear relationship between particle size and load to failure.

This example demonstrates that the samples made according to the present invention consistently crush at critical loads well below 1 N.

Example 3

This example demonstrates the efficacy of a granular composition versus either a paste or a dust formulation. In each test, ten male german cockroaches were exposed to the test formulation and then transferred to another location with alternate food and water. Mortality was recorded daily, and each test was replicated three times.

Figure 4:
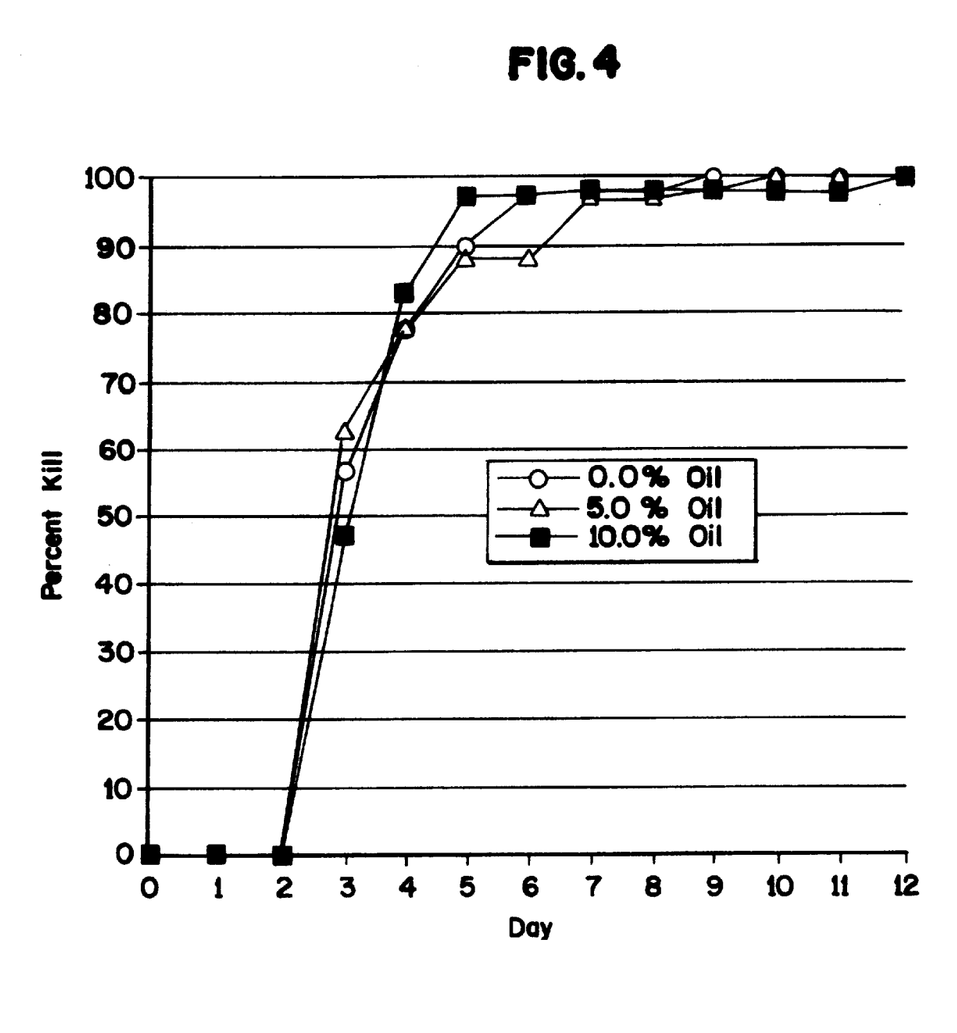
FIG. 4 is a plot of kill percent versus time for several granular formulations of the present invention.

FIG. 4 shows the efficacy of a 54 wt-% boric acid composition, tested at three different oil contents. All three formulations achieved nearly a 100 percent kill rate within about 5 days.

Figure 5:
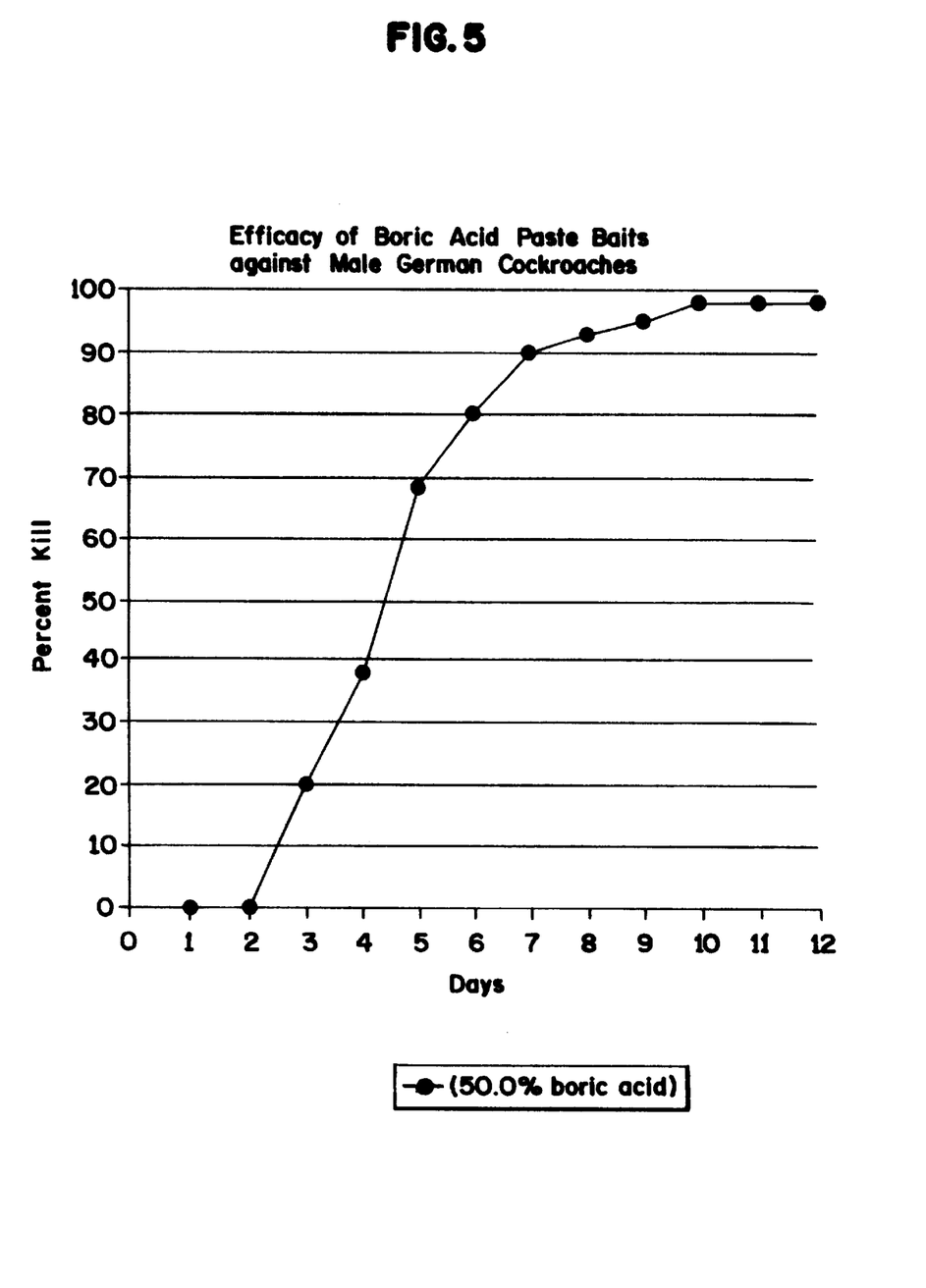
FIG. 5 is a plot of kill percent versus time for a boric acid paste formulation.
Figure 6:
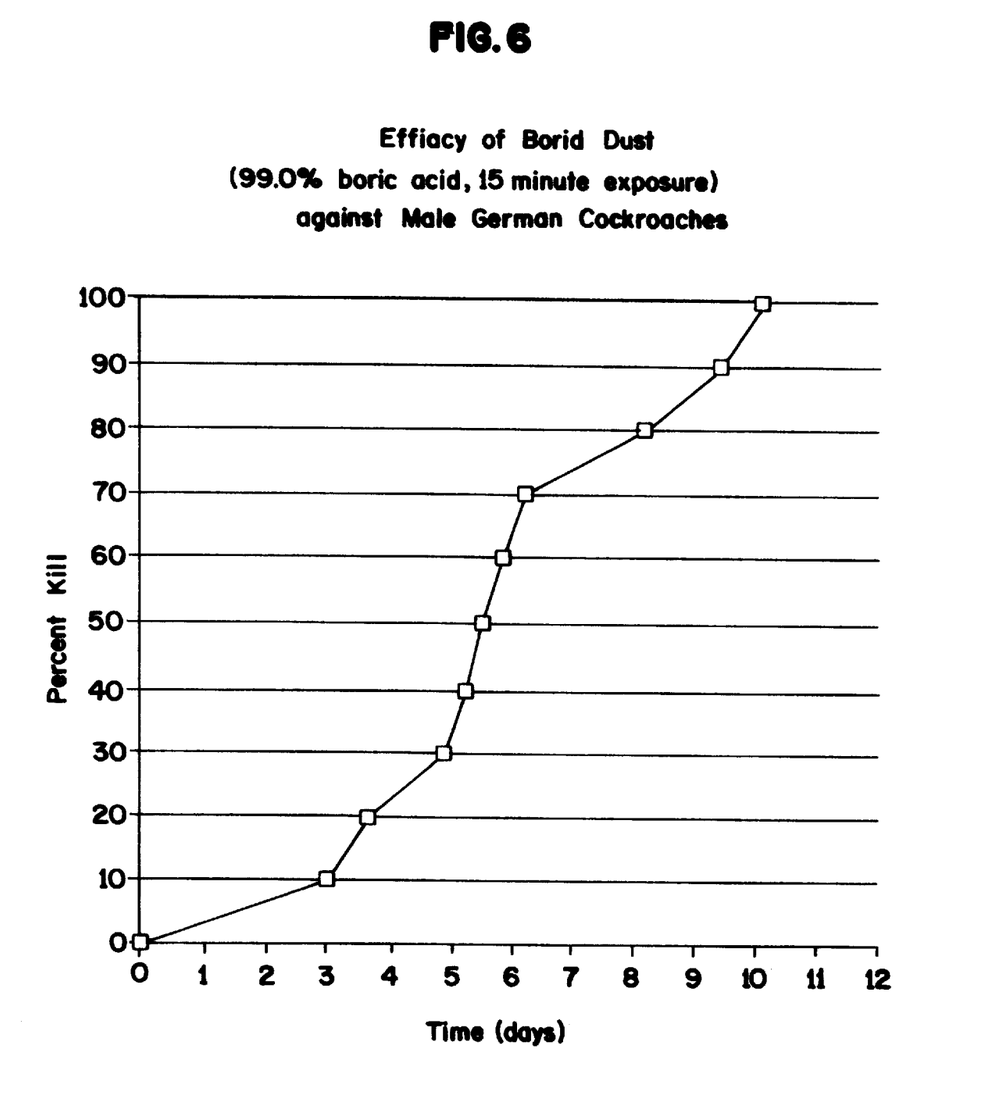
FIG. 6 is a plot of kill percent versus time for a boric acid dust formulation.

FIG. 5 describes the kill results of a boric acid paste composition made according to U.S. Pat. No. 4,988,511, which is hereby incorporated by reference herein. In this case, nearly 10 days are required to achieve a kill rate in excess of 90 percent. FIG. 6 also demonstrates a required 10 day period for a 99% boric acid dust formulation. This formulation is essentially pure boric acid. In this test, a 15 minute exposure time was used.

These results show conclusively that for similar chemical compositions, a granular formulation is substantially faster and more effective at killing cockroaches.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A substantially water-free granular insecticide composition produced by the following process steps:

(a) combining and blending an insecticidally effective amount of boric acid or acephate with a feeding stimulant comprising a carbohydrate and protein;

(b) granulating the blend of step (a) to granules of a desired size in diameter; and (c) slowly adding a lipid to said granules while mixing;

wherein the amount of lipid added in step (c) is not greater than about 25 wt-% but greater than 0 wt-%, based on the total weight of the granules, wherein said desired size in diameter in step (b) is sufficient to provide the resultant granule in step (c) with a diameter size in the range of from about 0.4 to about 2.0 millimeters, and wherein said resultant granule in step (c) has a critical load when crushed to less than 1 Newton.

2. The composition of claim 1, wherein the lipid is a vegetable oil.

3. The composition of claim 2, wherein the vegetable oil is soybean oil.

4. The composition of claim 1, wherein the carbohydrate is sucrose.

5. The composition of claim 4, wherein the sucrose is powdered.

6. The composition of claim 1, wherein the protein is milk solids.

7. The substantially water-free granular insecticide composition according to claim 1, wherein the amount of boric acid is about 40–60 wt-% based on the total weight of the granules.

8. The substantially water-free granular insecticide composition according to claim 7, wherein the lipid is a vegetable oil, the amount of said vegetable oil is about 5–15 wt-% based on the total weight of the granules, the carbohydrate is powdered sugar and the protein is milk solids.

9. The substantially water-free granular insecticide composition according to claim 1, wherein the amount of acephate is about 0.1 to 5 wt-% based on the total weight of the granules.

10. The substantially water-free granular insecticide composition according to claim 9, wherein the lipid is a vegetable oil, the amount of said vegetable oil is about 5–15 wt-% based on the total weight of the granules, the carbohydrate is powdered sugar and the protein is milk solids.

11. The method of controlling insect pests comprising applying to areas to be controlled an effective amount of a substantially water-free composition according to claim 1.

12. The method of claim 11, wherein the composition is applied in moist or wet areas.

13. The method of claim 11, wherein the composition is applied in hot, dry areas.

14. The method of controlling insect pests comprising applying to areas to be controlled an effective amount of a substantially water-free composition according to claim 7.

15. The method of claim 14, wherein the composition is applied in moist or wet areas.

16. The method of claim 14, wherein the composition is applied in hot, dry areas.

17. The method of controlling insect pests comprising applying to areas to be controlled an effective amount of a substantially water-free composition according to claim 9.

18. The method of claim 17, wherein the composition is applied in moist or wet areas.

19. The method of claim 17, wherein the composition is applied in hot, dry areas.

* * * * *